(12) United States Patent
 Ratcliff (10) Patent No.: US 11,904,102 B2
(45) Date of Patent: Feb. 20, 2024

(54) METHOD AND SYSTEM FOR APPLYING ADAPTED COLOUR RENDERING ON A DISPLAY

(71) Applicant: TOBII AB, Danderyd (SE)

(72) Inventor: Andrew Ratcliff, Danderyd (SE)

(73) Assignee: Tobii AB, Danderyd (SE)

(*) Notice: Subject to any disclaimer, the term of this patent is extended or adjusted under 35 U.S.C. 154(b) by 0 days.

(21) Appl. No.: 17/757,687

(22) PCT Filed: Dec. 17, 2020

(86) PCT No.: PCT/EP2020/086655
§ 371 (c)(1),
(2) Date: Jun. 17, 2022

(87) PCT Pub. No.: WO2021/122902
PCT Pub. Date: Jun. 24, 2021

(65) Prior Publication Data
US 2023/0013533 A1    Jan. 19, 2023

(30) Foreign Application Priority Data
Dec. 17, 2019 (SE) .................... 1951480-1

(51) Int. Cl.
*G06F 3/01* (2006.01)
*A61M 21/00* (2006.01)
*G09G 3/00* (2006.01)

(52) U.S. Cl.
CPC ............ *A61M 21/00* (2013.01); *G06F 3/013* (2013.01); *G09G 3/002* (2013.01);
(Continued)

(58) Field of Classification Search
CPC ......... G06T 15/20; G06F 3/012; G06F 3/013; A61M 21/00; A61M 2021/005;
(Continued)

(56) References Cited

U.S. PATENT DOCUMENTS 9,316,834 B2 * 4/2016 Makino .............. G02B 27/0176
9,406,277 B1 * 8/2016 Letourneur .............. G09G 5/10
(Continued)

FOREIGN PATENT DOCUMENTS

| EP | 2172925 A1 | 4/2010 |
|----|------------|--------|
| EP | 2955648 A1 | 12/2015 |
| EP | 3561798 A1 | 10/2019 |

OTHER PUBLICATIONS

Swedish Search Report, dated Sep. 30, 2020, Stockholm, for application 1951480-1, Swedish Patent and Registration Office.
(Continued)

*Primary Examiner* — Mihir K Rayan
(74) *Attorney, Agent, or Firm* — Christopher Ignatius Moylan (57) ABSTRACT

A method for applying adapted colour rendering in relation to intensity of light of wavelengths relevant to the circadian rhythm of a user, a computer program, a carrier, a system and a head-mounted device is disclosed. The method comprises receiving gaze tracking information identifying a gaze vector of the user of the system, and determining a respective location of a first area of the display and a second areas of the display based on the identified gaze vector. A first colour rendering mode is applied in the first area of the display, and a second colour rendering mode is applied in the second area of the display. The first colour rendering mode and the second colour rendering mode differ in relation to a degree of selective adaptation of intensity of light of wavelengths relevant to the circadian rhythm of the user.

22 Claims, 7 Drawing Sheets

(52) U.S. Cl.
CPC .......... *A61M 2021/005* (2013.01); *G09G 2320/0666* (2013.01); *G09G 2354/00* (2013.01)

(58) Field of Classification Search
CPC .......... G09G 3/002; G09G 2320/0666; G09G 2354/00; G09G 2340/0464; G09G 5/02; G09G 2320/0693
See application file for complete search history.

(56) References Cited

U.S. PATENT DOCUMENTS

| | | | |
|---|---|---|---|
| 9,665,171 B1* | 5/2017 | Skogö | G06F 3/013 |
| 11,614,798 B2* | 3/2023 | Muehlhausen | G06F 3/013 345/156 |
| 2010/0264850 A1* | 10/2010 | Yamamoto | G09G 3/3208 315/312 |
| 2014/0104321 A1 | 4/2014 | Steffy et al. | |
| 2015/0269907 A1 | 9/2015 | Hadas et al. | |
| 2015/0356954 A1* | 12/2015 | Lee | G16H 40/63 345/173 |
| 2016/0267716 A1* | 9/2016 | Patel | G06F 3/013 |
| 2017/0205977 A1 | 7/2017 | Fertik et al. | |
| 2017/0235362 A1* | 8/2017 | Thunström | G06F 3/013 345/428 |
| 2018/0033405 A1* | 2/2018 | Tall | G06T 9/00 |
| 2018/0284451 A1* | 10/2018 | Eash | G09G 5/00 |
| 2019/0156793 A1* | 5/2019 | Sun | G09G 5/391 |
| 2021/0174768 A1* | 6/2021 | Jarvenpaa | G09G 5/37 |

OTHER PUBLICATIONS

European Search Report, dated Apr. 14, 2021, Munich, for application PCT/EP2020/0866655, European Patent Office.
Mantiuk et al., "Gaze-Dependent Tone Mapping," Jun. 26, 2023, Images Analysis and Recognition, Springer Berlin Heidelberg, ISBN: 978-3-642-39093-7, pp. 426-433.

* cited by examiner

METHOD AND SYSTEM FOR APPLYING ADAPTED COLOUR RENDERING ON A DISPLAY

CROSS-REFERENCE TO RELATED APPLICATIONS

This application is a national stage application, filed under 35 US.C. § 371, of International Application No. PCT/EP2020/086655, filed on Dec. 17, 2020, which claims the benefit of and priority to Swedish Application No. 1951480-1, filed on Dec. 17, 2019, the disclosures of which applications are herein incorporated by reference in their entirety for all purposes.

TECHNICAL FIELD

The present disclosure relates to the field of displays. In particular, the present disclosure relates to methods and systems for applying adapted colour rendering in relation to intensity of light of wavelengths relevant to the circadian rhythm.

BACKGROUND

Disturbance of the circadian rhythm of a person is detrimental from several points of view. For example, there are indications that such a disturbance may contribute to several diseases and symptoms such as Myocardial infarction, Sepsis, cancer, Arrhythmias, Diabetes Obesity Metabolic Syndrome, immune dysregulation, reproductive problems, sleep deprivation, learning deficits, depression, mood swings, disrupted body temperature management and more.

In order to control or affect the circadian rhythm, different solutions have been suggested in respect to displays where the intensity of light of wavelengths relevant to the circadian rhythm is adapted. The solutions are associated with different imperfections and deficiencies. For example adapting the intensity of wavelengths relevant to the circadian rhythm (mainly blue light) in a display will provide a colour rendering in the display that may be perceived as distorted and/or unnatural to a user.

In addition to the above diseases and symptoms, there are indications that lack of exposure to light of wavelength relevant to the circadian rhythm contributes to Myopia (short sightedness).

Addressing the above-identified issues in the art is desirable.

SUMMARY

An object of the present disclosure is to mitigate, alleviate, or eliminate one or more of the deficiencies in the art and disadvantages singly or in any combination.

This object is obtained by a method, a system, a computer program, and a carrier according to the accompanying independent claims.

The dependent claims provide further advantageous features.

The present disclosure is at least partly based on the realization that it would be beneficial to enable differentiated adaptation of colour rendering in relation to light of wavelengths relevant for the circadian rhythm in different areas of the display in order to avoid or mitigate colour rendering resulting in an unnatural experience of colours for a user.

According to a first aspect, a method in a system comprising a display for applying adapted colour rendering in relation to intensity of light of wavelengths relevant to the circadian rhythm of a user of the system is provided. In the method, gaze tracking information is received identifying a gaze vector of a user of the system and a respective location of a first area of the display and a second area of the display is determined based on the identified gaze vector. A first colour rendering mode is applied in the first area of the display, and a second colour rendering mode is applied in the second area of the display. The first colour rendering mode and the second colour rendering mode differ in relation to a degree of selective adaptation of intensity of light of wavelengths relevant to the circadian rhythm of the user.

By providing the possibility to use different colour rendering modes in different areas of the display, the selective adaptation of intensity of light of the wavelengths relevant to the circadian rhythm can be made to a different degree in different areas.

By receiving gaze tracking information identifying a gaze vector of the user, a degree of selective adaptation of intensity of light of wavelengths relevant to the circadian rhythm in a specific area of the different areas can be based on where the specific area is located in relation to the gaze vector, i.e. where on the display the user is looking.

By "adaptation of intensity" is meant that the intensity is either amplified or suppressed (increased or decreased) to be higher or lower, respectively, than what it would have been with a colour rendering without adaptation.

By "selective adaptation" is meant that the intensity of light of the wavelengths relevant to the circadian rhythm can be made without any (or at least less) adaptation of light of other wavelengths, i.e. independently (or semi-independently) from the intensity of light of other wavelengths. Furthermore, "selective adaptation of intensity of light of wavelengths relevant to the circadian rhythm" is not meant to require adaptation of intensity of light of all wavelengths relevant to the circadian rhythm. Adaptation of intensity of light of at least a subset of the wavelengths relevant to the circadian rhythm would be sufficient.

Furthermore, "light of wavelengths relevant to circadian rhythm" is not meant to exclude that the light is adapted for the sole (or even main) purpose of affecting the circadian rhythm. The light of wavelengths relevant to circadian rhythm may be relevant also for other purposes. For example, the light of wavelengths relevant to circadian rhythm is also relevant to production of dopamine and melatonin by Ganglion cells in the human retina. Dopamine has a growth inhibiting effect of the eyeball. Reduction of dopamine may cause eyeball elongation that in turn may result in Myopia (short sightedness). Hence, increasing light relevant to circadian rhythm in a display may result in higher production of dopamine and hence reduced risk for Myopia.

The degree of the selective adaptation may be based on perceptibility of the selective adaptation to the user in different areas. This enables selective adaptation to a higher degree in one or more areas of the different areas where such a selective adaptation would be perceived to a lesser extent by the user and to a lower degree in one or more areas of the different areas where such a selective adaptation would be perceived to a higher extent by the user.

In embodiments, the respective degree of selective adaptation for the first area and the second area is based on an effect which selective adaptation of light of wavelengths relevant to the circadian rhythm will have on the circadian rhythm when projected on corresponding areas of a retina of an eye of the user.

In further embodiments, the respective degree of selective adaptation for the first area and the second area is based on an effect which selective adaptation of light of wavelengths relevant to the circadian rhythm will have on the production of dopamine and melatonin when projected on corresponding areas of a retina of an eye of the user.

In embodiments, the first area of the display is located inside a border angle from the gaze vector and the second area of the display located outside the border angle from the gaze vector. The second colour rendering mode then involves a higher degree of selective adaptation of intensity of light of wavelengths relevant to the circadian rhythm than the first colour rendering mode.

Ganglion cells in the retina of an eye that are sensitive to light of the wavelengths relevant to the circadian rhythm and will affect the circadian rhythm generally have a highest density in a portion of the retina outside an angle from a fovea of the retina. On the other hand, the cone cells that register colour of light generally have a highest density in a portion of the retina inside this angle and have a lower density in the portion outside the angle. Hence, by selecting the border angle such that light from the second area of the display located outside the border angle will be projected on the portion of the retina of the user's eye that includes a higher density of ganglion cells that are sensitive to light of the wavelengths relevant to the circadian rhythm and will affect the circadian rhythm, a high effect on the circadian rhythm can be achieved. At the same time, since the cone cells that register colour of light have a lower density in that portion of the retina, the user will perceive the higher degree of selective adaptation of the second area of the display less than if the higher degree of selective adaptation would have been in the first area of the display from which light will be projected on the portion of the retina of the user's eye that includes a higher density of cone cells that register colour of light.

Furthermore, ganglion cells in the retina of the eye affect the production of dopamine and melatonin when exposed to light. Hence, by selecting the border angle such that light from the second area of the display located outside the border angle will be projected on the portion of the retina of the user's eye where the ganglion cells have a higher density, a high effect on the production of dopamine and melatonin can be achieved.

In some embodiments, the first colour rendering mode applied in the first area of the display located inside the border angle from the gaze vector involves no selective adaptation of intensity of light of wavelengths relevant to the circadian rhythm.

Since the border angle is generally selected such that light from the second area of the display located outside the border angle will be projected on the portion of the retina in which ganglion cells have a higher density and in which cone cells that register colour of light have a lower density, the first area of the display will be projected on a portion of the retina in which cone cells have a higher density. Hence, by applying the first colour rendering mode in the first area involving no selective adaptation of intensity of light of wavelengths relevant to the circadian rhythm, the user will have non-adapted colour rendering in the first area of the display which corresponds projected on the fourth portion of the retina most relevant in relation to colour registration.

In some embodiments, the first area is an entire area of the display inside the border angle from the gaze vector.

In some embodiments, the second area is an entire area of the display outside the border angle from the gaze vector.

In other embodiments, the second area is an area of the display outside the border angle from the gaze vector and inside an outer angle from the gaze vector larger than the border angle.

The density of ganglion cells is highest around a peak angle from the fovea. The second area can then be defined as an area of the display between the boarder angle and an outer angle larger than the border angle corresponding to a portion of the retina around the peak angle.

In further embodiments, the second colour rendering mode outside the border angle involves selective adaptation of the intensity of light of wavelengths relevant to the circadian rhythm to a largest degree at a peak angle from the gaze vector larger than the border angle.

Since the density of ganglion cells is highest around a peak angle from the fovea, the second colour rendering mode in the second area can then be selected to have a largest degree of adaptation at an angle corresponding to the peak angle.

The outer angle may be within the range 10-90°, preferably 15-60°.

The peak angle may be within the range 2-5°, more precise about 3.5°.

The border angle may be within the range 0.5-15°, preferably within the range 1-10°, more preferably within the range 2-6°.

In embodiments, the method further comprises applying a smooth transition from the first colour rendering mode to the second colour rendering mode along a border between the first area and the second area, on condition that the first area and the second area are adjacent to each other.

By providing a smooth transition, for example by using a gradual transition from a first degree of adaptation of the first colour rendering mode to a second degree of adaptation of the second colour rendering mode in an area between the first area and the second area, the border between the first area and the second area will not be as salient to the user.

In some embodiments, selective adaptation of intensity of light of wavelengths relevant to the circadian rhythm involves selective increase of intensity during daytime and/or selective decrease of intensity during nighttime.

Depending on the application and the intentions, the adaptation of intensity of light of wavelengths relevant to the circadian rhythm may vary. For applications only used during daytime, increase of intensity may be sufficient. Furthermore, when the intention is to avoid Myopia due to low production of dopamine by ganglion cells, increase of intensity during daytime may be sufficient. For applications only used during nighttime, decrease of intensity may be sufficient. For applications used both during daytime and nighttime, and intended to decrease of intensity may be sufficient.

Selective adaptation of intensity of light may be of some or all wavelengths within the range 280-500 nanometre, preferably within the range 440-490 nanometre.

According to a second aspect, a computer program comprising instructions is provided, which, when executed by a processor, cause at least one processor to perform the method of the first aspect.

Embodiments of the computer program according to the second aspect may for example include features corresponding to the features of any of the embodiments of the method according to the first aspect.

According to a third aspect, a carrier is provided comprising a computer program according to the second aspect, wherein the carrier is one of an electronic signal, optical signal, radio signal, and a computer readable storage medium.

Embodiments of the carrier according to the third aspect may for example include features corresponding to the features of any of the embodiments of the computer program according to the second aspect.

According to a fourth aspect, a system for applying adapted colour rendering in relation to intensity of light of wavelengths relevant to the circadian rhythm of a user of the system is provided. The system comprises a display, a processor, and a memory. The memory contains instructions executable by said processor, whereby said system is operative to receive gaze tracking information identifying a gaze vector of the user of the system and determining a respective location of a first area of the display and a second area of the display; apply a first colour rendering mode in the first area of the display, and apply a second colour rendering mode in the second area of the display. The first colour rendering mode and the second colour rendering mode differ in relation to a degree of selective adaptation of intensity of light of wavelengths relevant to the circadian rhythm of the user based on a respective location of the first area and the second area in relation to the gaze vector.

In embodiments, the respective degree of selective adaptation for the first area and the second area is based on an effect that selective adaptation of light of wavelengths relevant to the circadian rhythm will have on the circadian rhythm when projected on corresponding areas of a retina of an eye of the user.

In further embodiments, the respective degree of selective adaptation for the first area and the second area is based on an effect which selective adaptation of light of wavelengths relevant to the circadian rhythm will have on the production of dopamine and melatonin when projected on corresponding areas of a retina of an eye of the user.

In further embodiments, the first area of the display is located inside a border angle from the gaze vector and the second area of the display is located outside the border angle from the gaze vector. The second colour rendering mode then involves a higher degree of selective adaptation of intensity of light of wavelengths relevant to the circadian rhythm than the first colour rendering mode.

Further embodiments of the system according to the fourth aspect may for example include features corresponding to the features of any of the embodiments of the method according to the first aspect.

According to a fifth aspect, a head-mounted device is provided comprising a system according to the fourth aspect.

Embodiments of the head-mounted device according to the fifth aspect may for example include features corresponding to the features of any of the embodiments of the system according to the fourth aspect.

BRIEF DESCRIPTION OF THE DRAWINGS

The foregoing will be apparent from the following more particular description of the example embodiments, as illustrated in the accompanying drawings in which like reference characters refer to the same parts throughout the different views. The drawings are not necessarily to scale, emphasis instead being placed upon illustrating the example embodiments.

All the figures are schematic, not necessarily to scale, and generally only show parts which are necessary in order to elucidate the respective example, whereas other parts may be omitted or merely suggested.

DETAILED DESCRIPTION

Aspects of the present disclosure will be described more fully hereinafter with reference to the accompanying drawings. The apparatus and method disclosed herein can, however, be realized in many different forms and should not be construed as being limited to the aspects set forth herein. Like numbers in the drawings refer to like elements throughout.

The terminology used herein is for the purpose of describing particular aspects of the disclosure only, and is not intended to limit the invention. As used herein, the singular forms "a", "an" and "the" are intended to include the plural forms as well, unless the context clearly indicates otherwise.

In a retina of a human eye, there are two different types of photoreceptor cells, namely rod cells and cone cells. The rod cells are more sensitive to light than cone cells and are hence relevant in relation to low light (night) vision. Different cone cells are able to react differently to light of different wavelengths and are hence relevant in relation to colour vision.

Figure 1A:
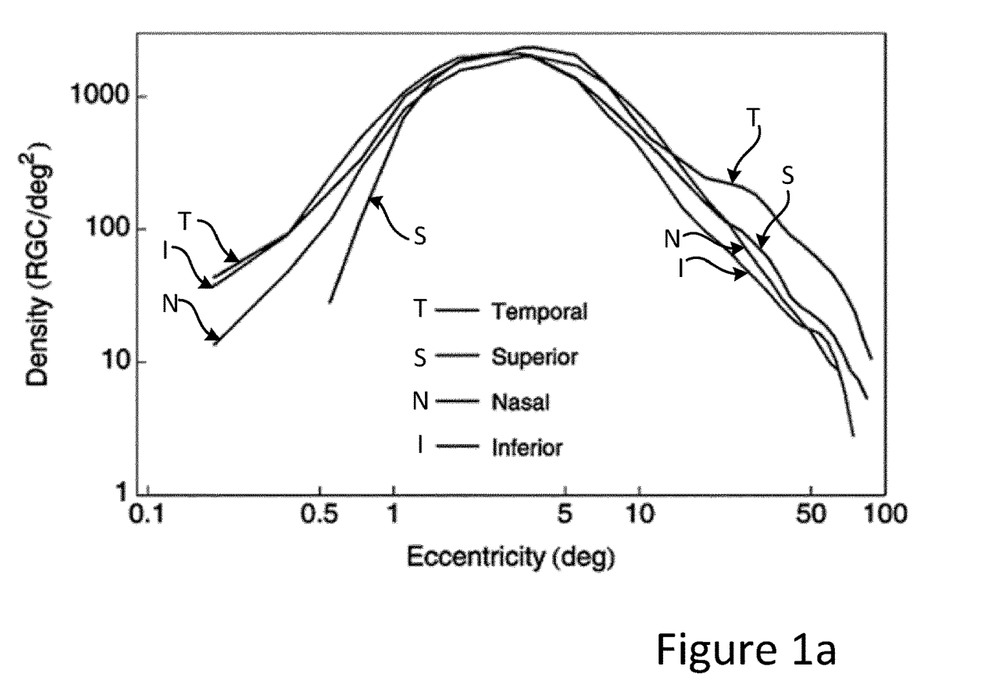
FIGS. 1a-c are diagrams showing the density of ganglion cells and cone cells in relation to angle from the fovea of an eye.
Figure 1B:
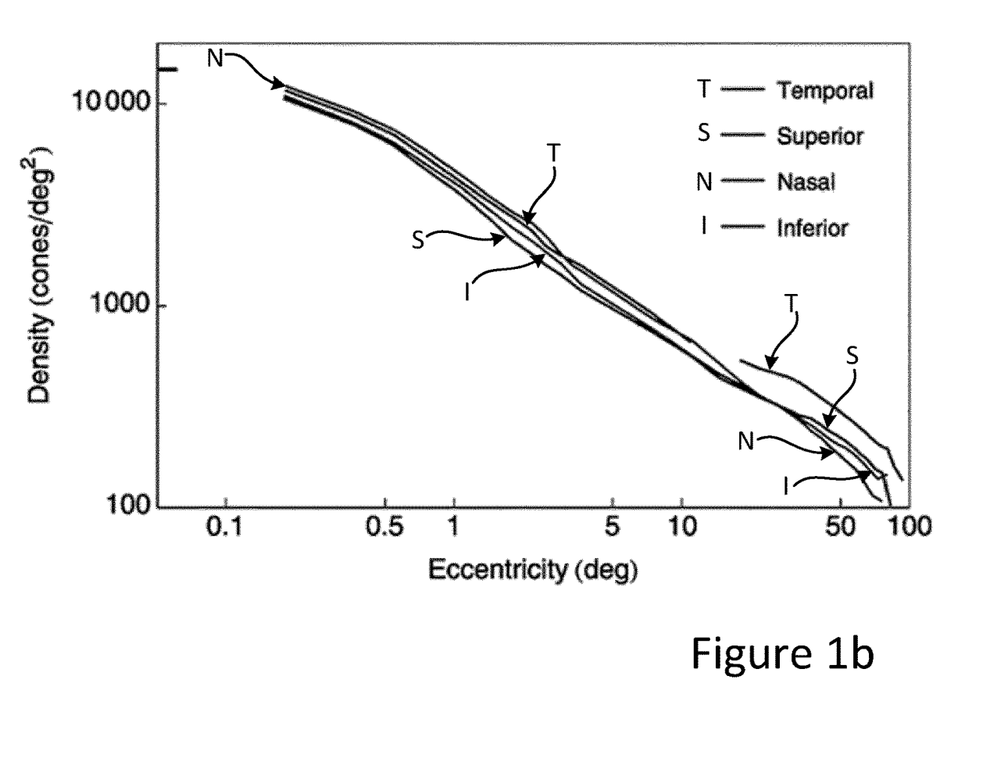

FIG. 1a is a diagram showing in logarithmic scale the density of ganglion cells in relation to angle from fovea of an eye in temporal, superior, nasal and interior direction. As can be seen in the diagram, the density (number of cells per $deg^2$) of ganglion cells increases with an angle from the fovea up to a maximum at approximately 3.5° from the fovea and then decreases again at larger angles. The increase is similar in all the direction. FIG. 1b is a diagram showing in logarithmic scale the density of cone cells in relation to angle from fovea of an eye. The density (number of cells per $deg^2$) of cone cells on the other hand, is highest very close to the centre of the fovea and is rapidly reduced at a rather small angle from the centre of the fovea. For example, at 5° from the fovea the density has decreased to approximately a tenth of the density as compared to the peak at approximately 0.2° from the fovea.

Figure 2:
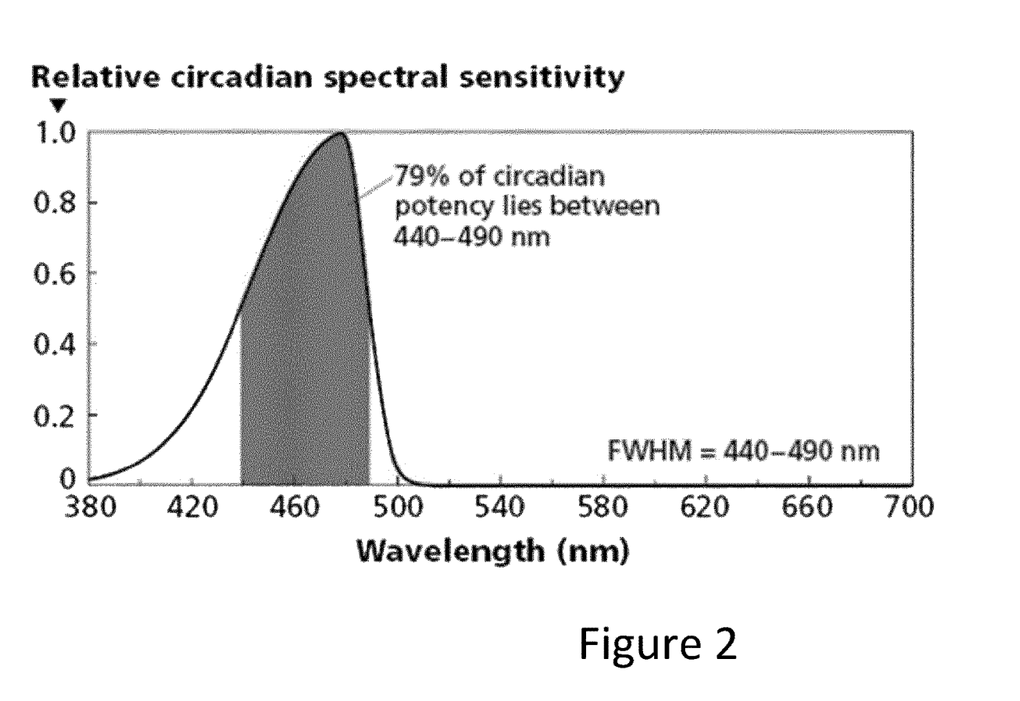
FIG. 2 is a diagram is a diagram showing the relative circadian spectral sensitivity in relation to wavelengths.

FIG. 2 is a diagram is a diagram showing the relative circadian spectral sensitivity in relation to wavelengths. Normalized to 1 at the maximum circadian spectral sensitivity at a little less than 480 nm, it can be seen from the diagram that virtually all of the circadian potency, i.e. ability to affect circadian rhythm, is provided by light of wavelengths between 380 and 500 nm. About 79% of the circadian potency is provided by light of wavelengths between 440 and 490 nm.

Ganglion cells have a sensitivity that is highest for light of the wavelengths relevant to the circadian rhythm and will affect the circadian rhythm when activated. Furthermore, as can be seen in FIG. 1a, the ganglion cells generally have a higher density in a portion of the retina outside an angle from a fovea of the retina. At the same time, in this portion of the retina, the cone cells that register colour of light generally have a lower density. Hence, if light of wavelengths relevant to the circadian rhythm is projected on the portion of the retina of the user's eye where the ganglion cells have a higher density, a high effect on the circadian rhythm can be achieved. At the same time, since the cone cells that register colour of light have a lower density in that portion of the retina, the user will not perceive, or at least perceive to a low degree, that the light has any particular colour.

Furthermore, ganglion cells in the retina of the eye affect the circadian rhythm by affecting the production of dopamine and melatonin when exposed to light. Hence, if light of wavelengths relevant to the circadian rhythm is projected on the portion of the retina of the user's eye where the ganglion cells have a higher density, a high effect on the production of dopamine and melatonin can be achieved. At the same time, since the cone cells that register colour of light have a lower density in that portion of the retina, the user will not perceive, or at least perceive to a lower degree, that the light has any particular colour.

In respect to an eye of a user, projection of light of wavelengths relevant to the circadian rhythm in a portion of a retina of the eye outside an angle from the fovea can be achieved by using eye tracking to identify a gaze vector of the user and then, based on the gaze vector, illuminate the eye in such a way that the light is projected on the portion of the retina outside the angle from the fovea. For example, in a system including a display, an area of the display outside a corresponding angle from the gaze vector can be adapted such that the light of wavelengths relevant to the circadian rhythm is either amplified or suppressed in that area of the display.

In a typical application, the colour of light in a display is provided to create a desired colour experience for the user. For example, in an image, film or game animation shown on the display, natural colours or colours achieving a particular mood may be desired. If the colour of light is then adapted such that light of wavelengths relevant to circadian rhythm is either increased or decreased, the desired colour experience will typically not be achieved.

By adapting an area of the display outside a corresponding angle from the gaze vector such that the light of wavelengths relevant to the circadian rhythm is illuminated from that area of the display, the light of the relevant wavelengths can be provided to a higher or lower than nominal intensity. This is due to the fact that the cone cells that register colour of light have a very low density in the portion of the retina onto which the adapted light in relation to the wavelengths relevant to circadian rhythm will be projected. Hence, the user will not perceive that the light has any particular adapted colour.

Figure 3A:
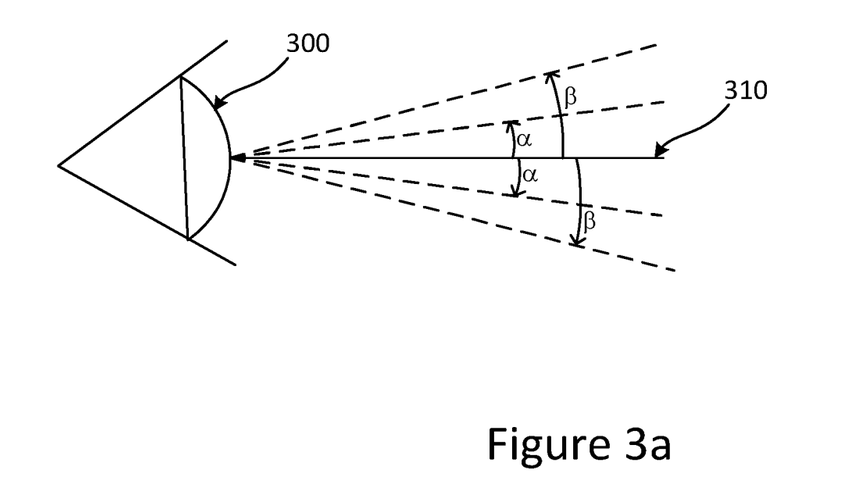
FIGS. 3a and 3b are schematic illustrations of a user's eye and a display in relation to embodiments of a system according to the present disclosure.
Figure 3B:
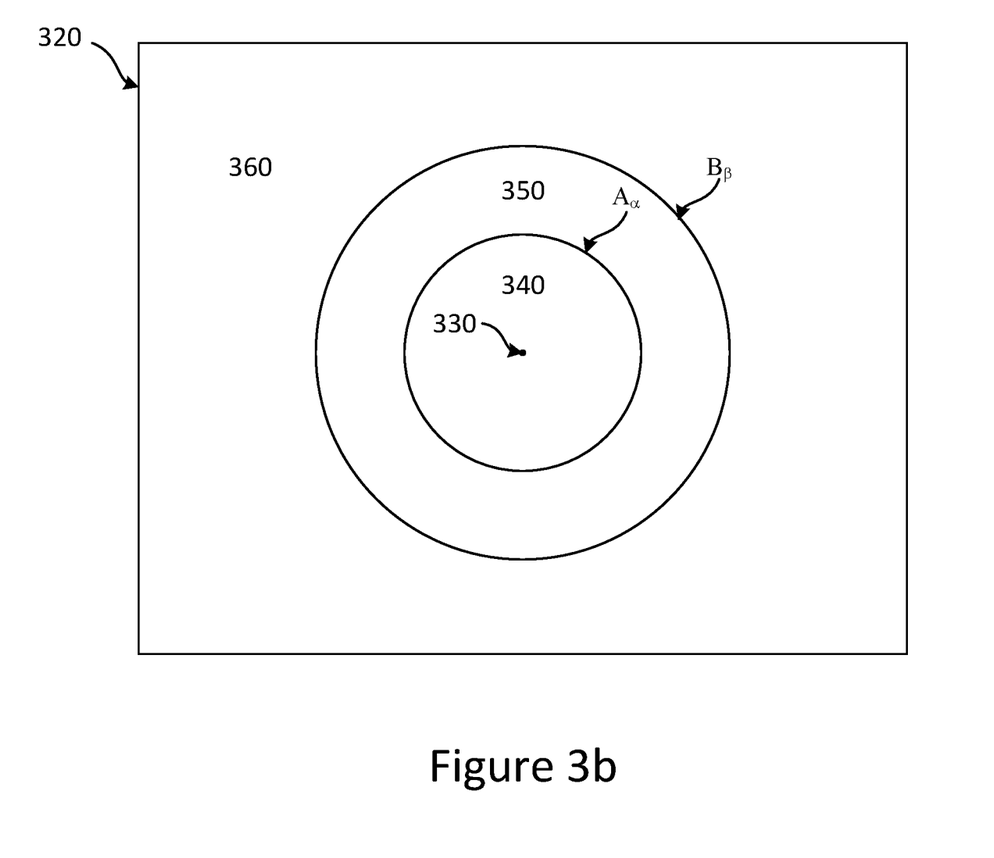

FIGS. 3a and 3b are schematic illustrations of a user's eye and a display in relation to embodiments of a system according to the present disclosure. Specifically, FIG. 3a discloses a user's eye 300 together with a gaze vector 310 in cross section. Light illuminated towards the eye 300 inside a border angle α, will be projected on a portion of the retina inside a corresponding angle from the fovea, and light illuminated towards the eye 300 outside the border angle α and inside an outer angle β, will be projected on a portion of the retina between corresponding angles from the fovea. Turning to FIG. 3b, a schematic illustration of a display 320 is shown. Based on the gaze vector 310, border angle α, and the outer angle β as illustrated in FIG. 3a, if the user's gaze vector is directed at a point 330 on the display 320, i.e. the user is looking at point 330, and the user's eye 300 is at a given distance from the display, a border circle (or a border ellipse if gaze vector is not parallel to the normal of the display plane of the display) $A_α$ will correspond to the border angle α, and an outer circle (or an outer ellipse if gaze vector is not parallel to the normal of the display plane of the display) $B_β$ will correspond to the outer angle β. Hence, light illuminated from the display towards the eye 300 from a first area 340 inside the border circle $A_α$ corresponding to the border angle α, will be projected on the portion of the retina inside the corresponding angle from the fovea, and light illuminated towards the eye 300 from a second area 350 outside the border circle $A_α$ and inside the outer circle $B_β$ corresponding to the outer angle β, will be projected on the portion of the retina between the corresponding angles from the fovea.

In addition to the border angle α and the outer angle β, a peak angle can be identified for which light of wavelengths relevant to the circadian rhythm will affect the circadian rhythm the most. This is an angle in relation to the gaze vector 310 from which light is projected in a portion of the retina corresponding to an angle from the fovea where the density of ganglion cells is highest. Generally, the border angle α and the outer angle β will be defined such that the peak angle is between the two angles.

Light towards the eye 300, e.g. from the display 320, at a given angle from the gaze vector 310 will generally be projected on the retina at a same or similar angle from the fovea. In the present disclosure, the border angle α, the outer angle β and the peak angle are defined in relation to the gaze vector 310 of light towards the eye 300, e.g. from the display 320. To any extent that an angle from the gaze vector 310 of light towards the eye 300 differs from the angle from the fovea on the retina the light is projected, the border angle α, the outer angle β and the peak angle in relation to the gaze vector 310 should be adapted such that light is projected at a desired area of the retina.

Figure 1C:
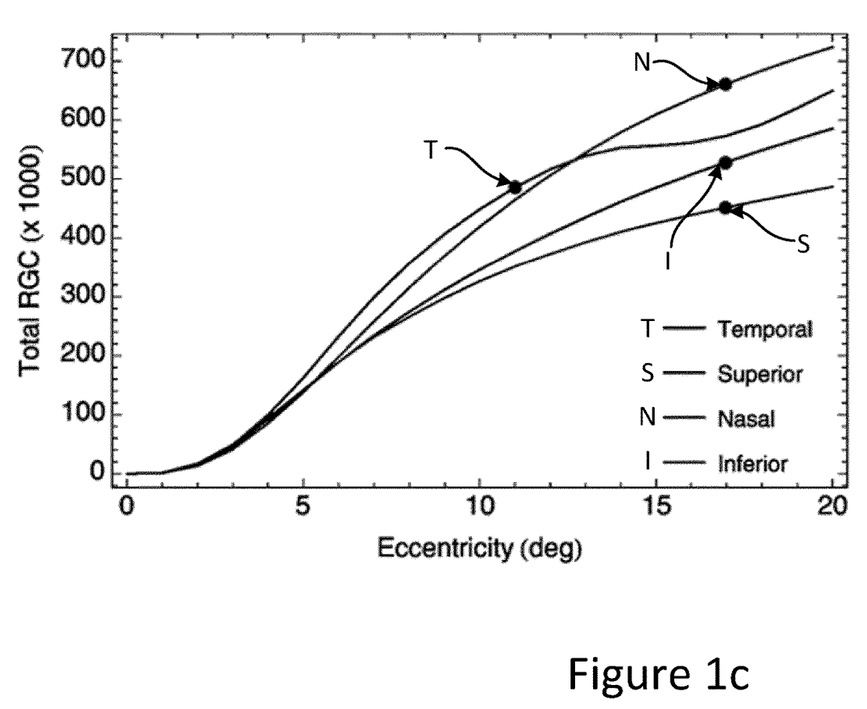

From FIGS. 1a and 1c showing the ganglion cell density distribution (peak and cumulative, respectively), and FIG. 1b showing cone cell density distribution it is possible to draw the following approximate conclusions:

if suppressing or amplifying light of wavelengths relevant to the circadian rhythm at 10° and more (border angle α=10°), about 50-80% of the ganglion cells are affected;

if suppressing or amplifying light of wavelengths relevant to the circadian rhythm at 5° and more (border angle α=5°) is blocked, about 70-95% of the ganglion cells are affected but the user may be aware that the suppressing or amplifying outside the border angle α;

if suppressing or amplifying light of wavelengths relevant to the circadian rhythm at 2° and more (border angle α=2°), over 95% of the ganglion cells will be affected, but the user will probably be aware of the suppressing or amplifying outside the border angle α.

Hence, the selection of the border angle α is a trade-off between affecting as much percentage of the ganglion cells and avoiding or reducing the user's perception of the adaptation by suppression or amplifying of light of wavelengths relevant to the circadian rhythm.

Figure 4A:
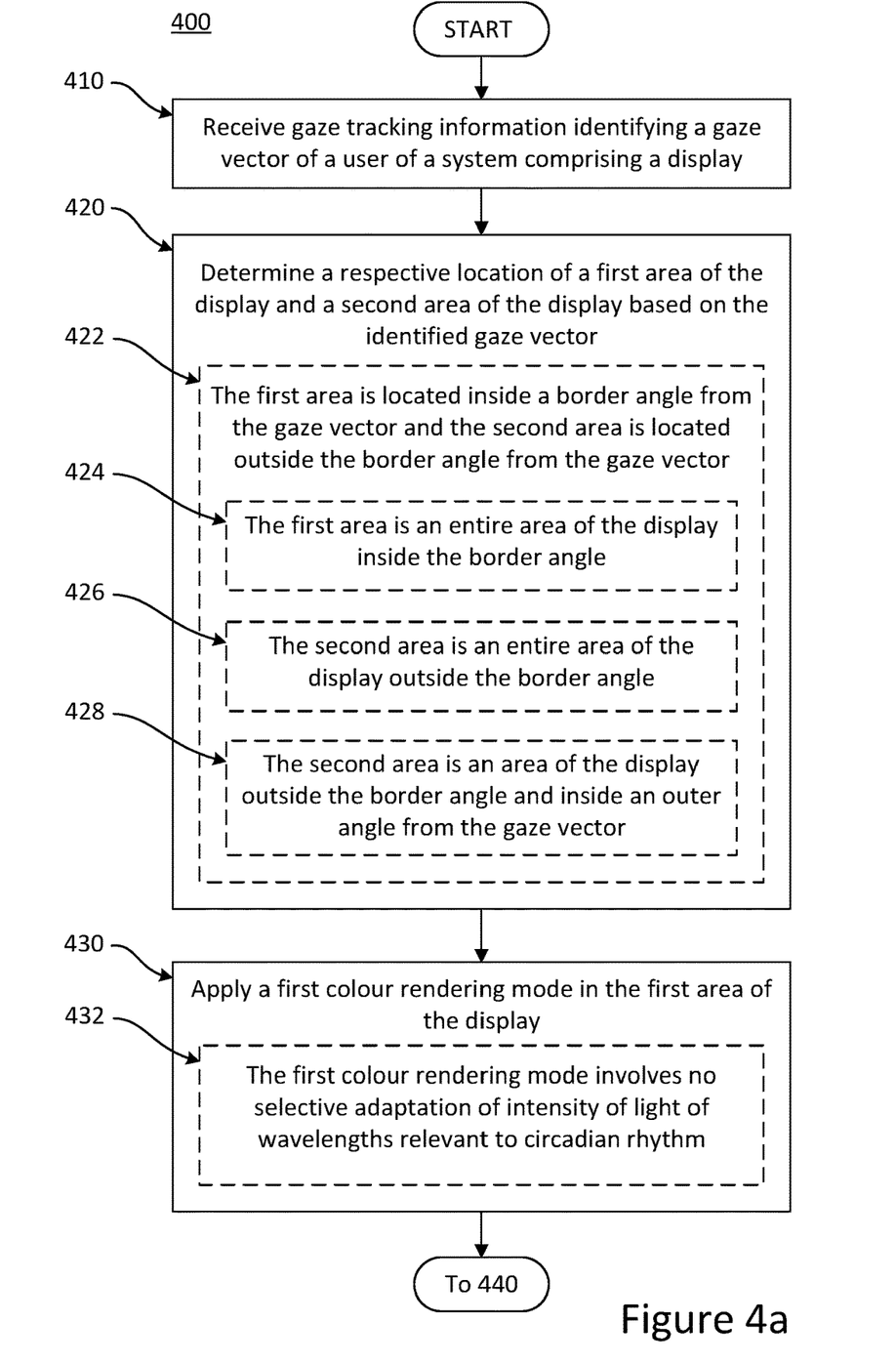
FIGS. 4a-c is a flowchart illustrating embodiments of a method according to the present disclosure.
Figure 4B:
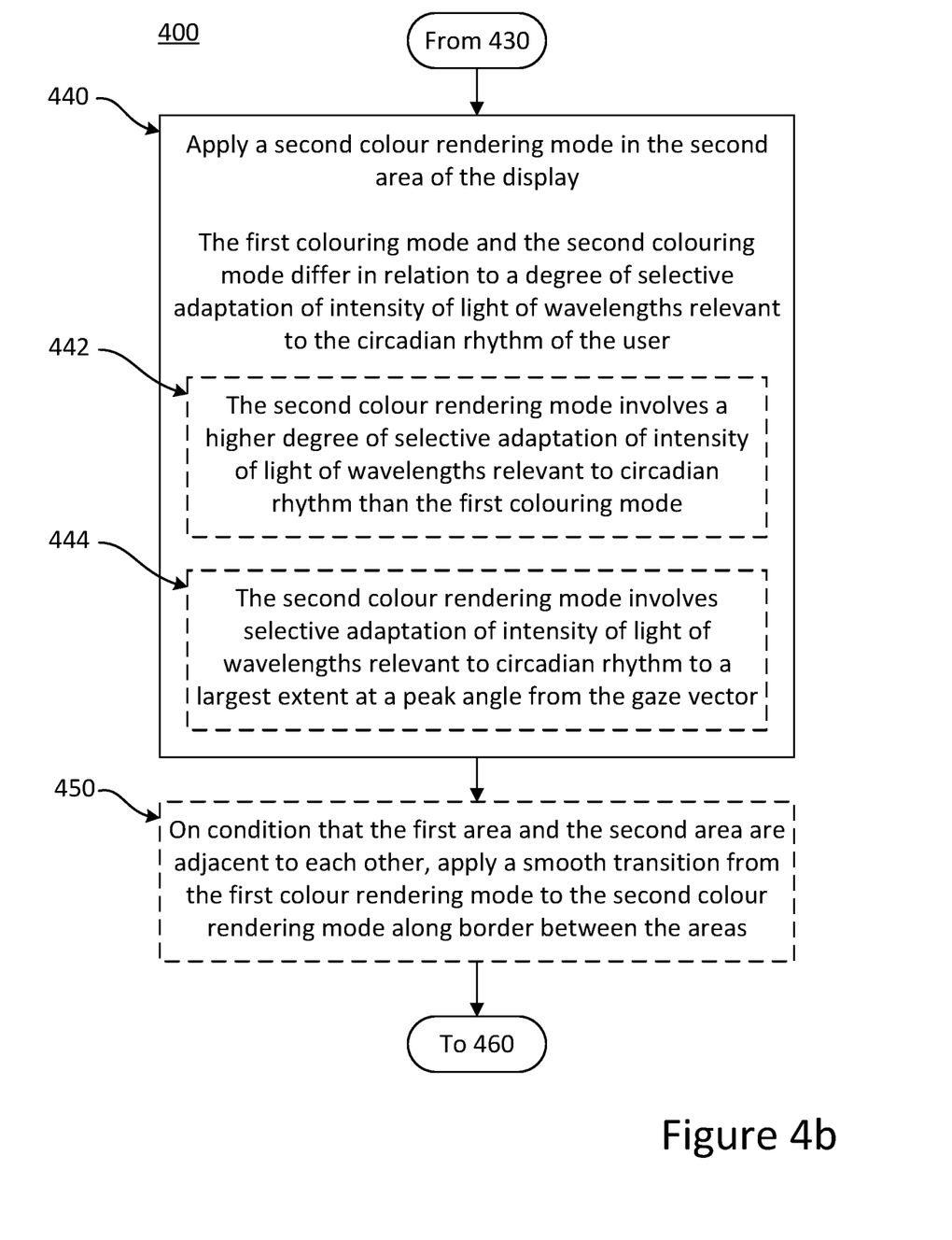
Figure 4C:
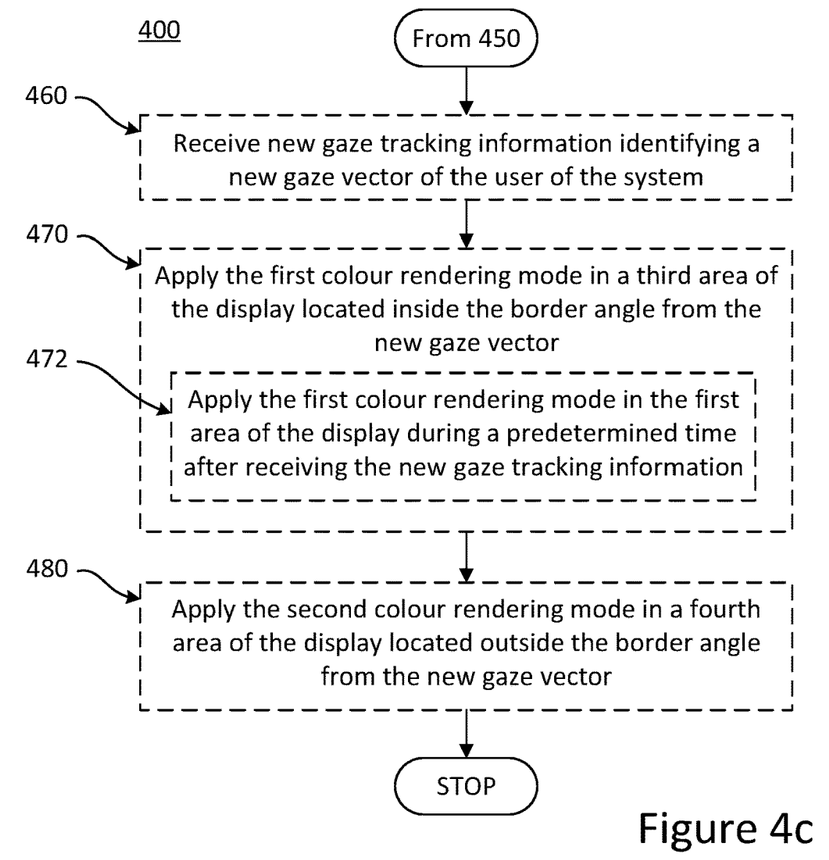

FIGS. 4a-c is a flowchart illustrating embodiments of a method according to the present disclosure. The method is performed in a system comprising a display and preferably also eye tracking functionality. By performing the methods, adapted colour rendering in relation to intensity of light of wavelengths relevant to the circadian rhythm of a user of the system is applied. First gaze tracking information identifying a gaze vector of the user of the system is received 410. The gaze tracking information is either received form eye tracking functionality internal to the system or from an entity external to the system. Based on the identified gaze vector, a respective location of a first area 340 of the display and a second area 350, 360 of the display are determined 420. A first colour rendering mode is applied 430 in the first area 340 of the display, and a second colour rendering mode is applied 440 in the second area 350, 360 of the display. The first colour rendering mode and the second colour rendering mode differ in relation to a degree of selective adaptation of intensity of light of wavelengths relevant to the circadian rhythm of the user.

The wavelengths in relation to which selectively adaptation of intensity is applied are within the range 380-500 nanometre, preferably within the range 440-490 nanometre.

When the intensity of light of wavelengths relevant to the circadian rhythm is selectively adapted, the intensity of light of other wavelengths are typically not adapted. Furthermore, it is not required to adapt intensity of light of all wavelengths relevant to the circadian rhythm. Adaptation of intensity of light of only a subset of the wavelengths relevant to the circadian rhythm could still provide useful results.

The intensity of light of wavelengths relevant to circadian rhythm is selectively adapted by either being amplified or suppressed (increased or decreased) to be higher or lower, respectively, than what it would have been with a colour rendering without adaptation, i.e. in relation to a nominal colour rendering. This is done to a higher degree in the second area 350, 360 than in the first area 340.

Generally, the respective degree of selective adaptation for the first area 340 and the second area 350, 360, is based on an effect that selective adaptation of light of wavelengths relevant to the circadian rhythm will have on the circadian rhythm when projected on corresponding areas of a retina of an eye of the user. Hence, the adaptation, e.g. by increasing or decreasing the intensity of light of the wavelengths relevant to the circadian rhythm, will be most in an area of the display which will be projected on a corresponding area of the retina of the eye of the user for which illumination or not by light of wavelengths relevant to the circadian rhythm will affect the circadian rhythm the most.

Typically, selective adaptation of intensity of light of wavelengths relevant to the circadian rhythm involves selective increase or amplification of intensity during daytime and selective decrease or suppressing of intensity during nighttime. This would for example normally be the case to promote the everyday circadian rhythm for a person staying the same time zone.

Alternative timing of the selective adaptation is also envisaged in order to promote the circadian rhythm. For example, for a person travelling to a time zone which is different form the time zone the person normally lives in, the selective adaptation can be made based on the timing of daytime and nighttime of the time zone the person normally lives in, in order to maintain the normal circadian rhythm. For such a case, selective adaptation may involve selective increase or amplification of intensity during daytime and selective decrease or suppressing of intensity during nighttime in relation to the time zone the person normally lives in and not in relation to the time zone the person is currently in in relation to a travelling.

As indicated in relation to FIGS. 1a-c, the sensitivity to wavelengths relevant to the circadian rhythm and the perception of colours varies with an angle from the fovea. More specifically, the border angle $\alpha 0$ can be identified outside which in the retina the density of ganglion cells sensitive to the wavelengths relevant to the circadian rhythm and/or production of dopamine and melatonin is comparably high and the density of cone cells that register colour of light is comparably low.

The first area 340 of the display may be located inside the border angle $\alpha$ from the gaze vector and the second area 350, 360 of the display may be located outside the border angle $\alpha$ from the gaze vector 422. Thus, light emitted from the first area 340 of the display will be projected onto the portion of the retina inside the border angle $\alpha$ (this corresponds to the area 340 of FIG. 3b). In this part of the retina, the density of ganglion cells sensitive to the wavelengths relevant to the circadian rhythm and/or production of dopamine and melatonin is lower and the density of cone cells that register colour of light is highest. Furthermore, light emitted from the second area 350, 360 of the display will be projected onto the portion of the retina outside the border angle $\alpha$ (this corresponds to the areas 350 and 360 of FIG. 3b). In this part of the retina, the density of ganglion cells sensitive to the wavelengths relevant to the circadian rhythm and/or production of dopamine and melatonin is highest and the density of cone cells that register colour of light is very low. Furthermore, the second colour rendering mode may then involve a higher degree of selective adaptation of intensity of light of wavelengths relevant to the circadian rhythm than the first colour rendering mode 442. The border angle $\alpha$ is within the range 0.5-15°, preferably within the range 1-10°, more preferably within the range 2-6°.

Although the method does not exclude selective adaptation of intensity of light of wavelengths relevant to the circadian rhythm in the first area 340, typically, the first colour rendering mode involves no such selective adaptation 432. This is because such selective adaptation would be perceptible to a user to a higher extent in the first area 340 since the light from that area will be projected onto the part of the retina the density of cells (cone cells) that register colour of light is highest.

The first area 340 may for example be the entire area of the display inside the border angle $\alpha$ from the gaze vector 424.

The second area 350, 360 may for example be the entire area of the display outside the border angle $\alpha$ from the gaze vector 426. In alternative 428, the second area 350 is an area of the display outside the border angle $\alpha$ from the gaze vector and inside the outer angle $\beta$ from the gaze vector (this corresponds to the area 350 of FIG. 3b), where the outer angle $\beta$ is larger than the border angle $\alpha$. The outer angle $\beta$ is within the range 10-90°, preferably within the range 15-60°.

Furthermore 444, in the second colour rendering mode, selective adaptation of the intensity of light of wavelengths relevant to the circadian rhythm may vary with the angle such that it is at a largest degree at a peak angle from the gaze vector larger than the border angle $\alpha$. The peak angle is within the range 2-5°, more precise about 3.5°.

Additionally, on condition that the first area 340 and the second area 350, 360 are adjacent to each other, a smooth transition from the first colour rendering mode to the second colour rendering mode along a border between the first area 340 and the second area 350, 360 may be applied 450. In one example, in a border area starting inside the border angle $\alpha$ and ending outside the border angle $\alpha$, the degree of selective adaptation is gradually increased from the defined degree of selective adaptation according to the first colour rendering mode to the defined degree of selective adaptation according to the second colour rendering mode. The smooth transition may be implemented in many ways. This is intended to make the transition from the first colour rendering mode in the first area 340 of the display and the second colour rendering mode in the second area 350, 360 of the display smoother and less salient.

When the user looks at another point of the display, the gaze vector of the user changes. When new gaze tracking information identifying a new gaze vector of the user of the system are received 460, the first colour rendering mode is applied 470 in a third area of the display located inside the border angle α from the new gaze vector, and the second colour rendering mode is applied 480 in a fourth area of the display located outside the border angle α from the new gaze vector.

In a first alternative, the first colour rendering mode and the second colour rendering mode are applied in the third area and the fourth area, respectively, as soon as the third area and the fourth area have been identified. Hence, the area of the display having the first colour rendering mode will be the border area inside the border angle α with the user gaze point in the middle that will follow the user's gaze. The area of the display outside the border angle will have the second colour rendering mode.

In a second alternative, the first colour rendering mode is applied in the third area as soon as the third area has been identified. Furthermore, the first colour rendering mode is maintained during a predetermined time after receiving the new gaze tracking information in the first area 340 of the display 320, 472 simultaneously with applying the first colour rendering mode in the third area of the display. During that predetermined time, the second colour rendering mode is applied in the portion of the fourth area that does not overlap with the first area 340 (and the third area). When the predetermined time has lapsed after receiving the new gaze tracking information, the first colour rendering mode is applied in the third area of the display and the second colour rendering mode is applied in the fourth area of the display. Hence, the area of the display having the first colour rendering mode will first be the border area inside the border angle α with the user gaze point in the middle. When the user changes gaze point, the border circle $A_\alpha$ will follow the user's gaze with a difference from the first alternative that the previous position of the border circle $A_\alpha$ will still have the first colour rendering mode for the predetermined time.

The second alternative may be used to reduce the risk that moving the gaze will cause a perceivable effect in the periphery of the user's field of view when an area of the display in which the first colour rendering mode was applied changes such that the second colour rendering mode is applied in it.

Figure 5:
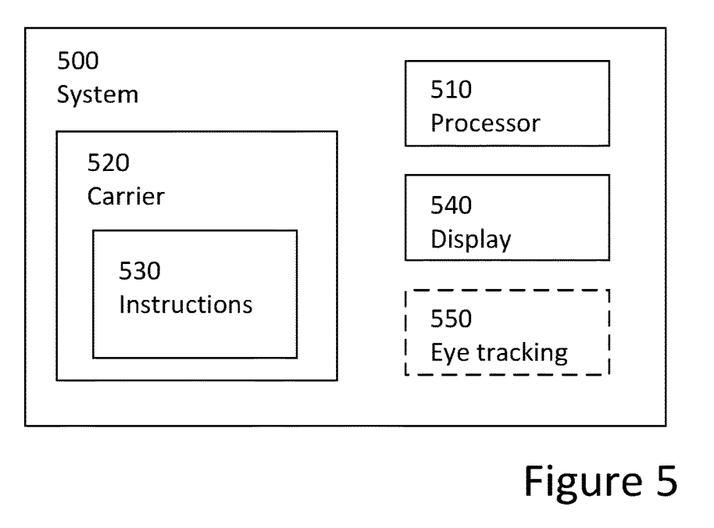
FIG. 5 is a block diagram illustrating embodiments of a system according to the present disclosure.

In FIG. 5, embodiments of a system 500 according to the present disclosure a system is disclosed. The system 500 is configured for applying adapted colour rendering in relation to intensity of light of wavelengths relevant to the circadian rhythm of a user, e.g. according to the embodiments of the method according to the present disclosure may be performed as disclosed in relation to FIGS. 4a, 4b and 4c. The system 500 comprises a processor 510, and a carrier 520 including computer executable instructions 530, e.g. in the form of a computer program, that, when executed by the processor 510, cause the system 500 to perform the method of the present disclosure, e.g. according to the embodiments disclosed in relation to FIGS. 4a, 4b and 4c. The carrier 520 may for example be an electronic signal, optical signal, radio signal, a transitory computer readable storage medium, and a non-transitory computer readable storage medium. The system 500 further comprises a display 540. The system further preferably includes internal eye tracking functionality 550. In alternative the eye tracking functionality may be located outside the system and the eye tracking information identifying a gaze vector of a user of the system is then received to the system from the outside the system, e.g. from a separate eye tracking system.

Figure 6A:
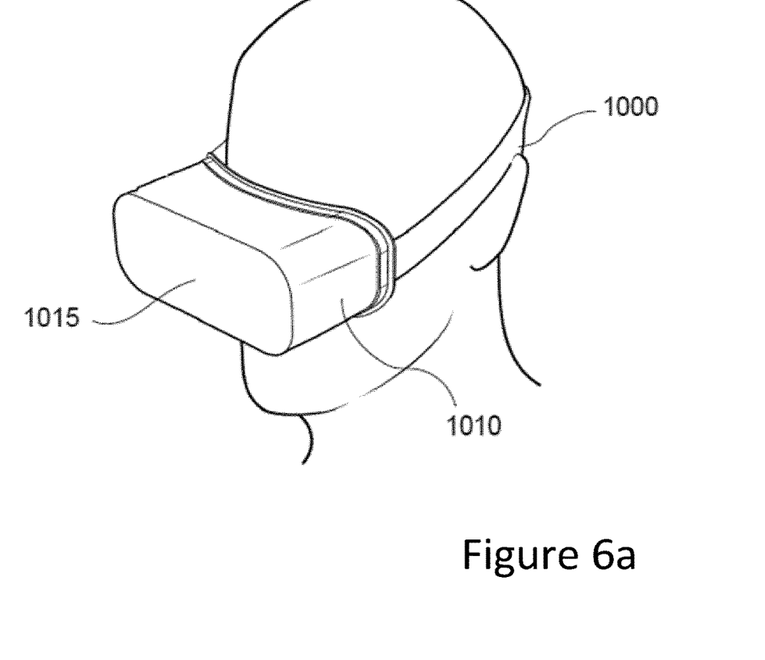
FIGS. 6a and 6b are schematic illustrations of embodiments of a head-mounted device and a remote display system, respectively, according to the present disclosure.
Figure 6B:
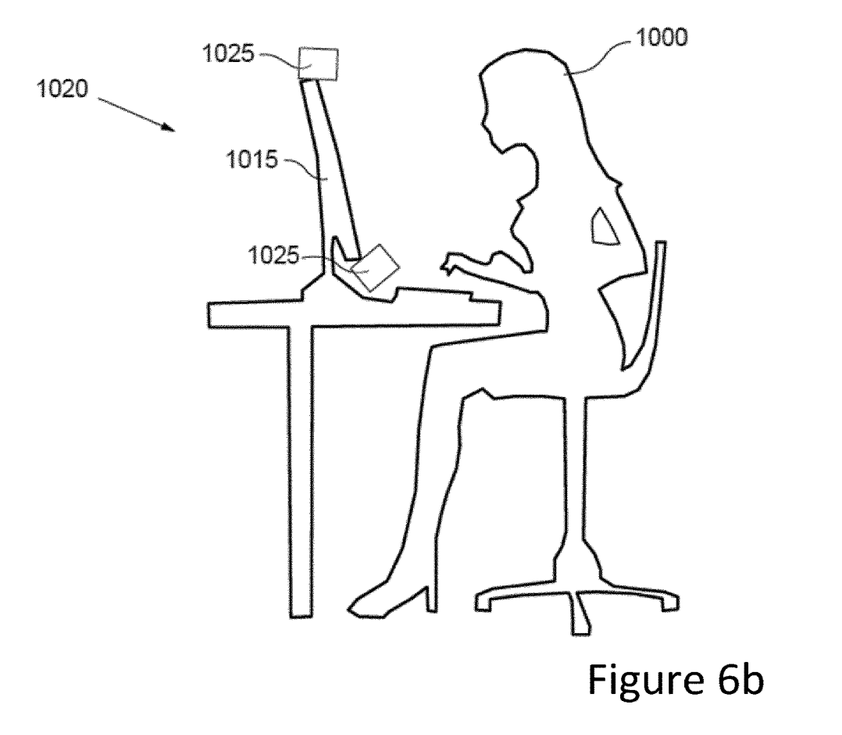

The system 500 as illustrated in relation to FIG. 5 may for example be implemented in a head-mounted device as illustrated in FIG. 6a or a remote display system as illustrated in FIG. 6b.

FIG. 6a shows a head-mounted device 1010 according to one or more embodiments. The head-mounted device 1010 is a device, which may optionally be adapted to be mounted (or arranged) at the head of a user 1000, as shown in FIG. 6a. The head-mounted device 1010 may e.g. comprise and/or be comprised in a head-mounted display, HMD, such as a virtual reality (VR) headset, an augmented reality (AR) headset or a mixed reality (MR) headset. The head-mounted device 1010 or HMD comprises a displaying device 1015. The displaying device 1015 may be transparent for real world experiences and non-transparent for virtual world experience. The head-mounted device 1010 is configured for applying adapted colour rendering in relation to intensity of light of wavelengths relevant to the circadian rhythm of a user, e.g. according to the embodiments of the method according to the present disclosure may be performed as disclosed in relation to FIGS. 4a, 4b and 4c. For example, the head-mounted device 1010 is configured to provide eye tracker functionality by a gaze tracking signal using one or more gaze tracking sensors (not shown), e.g. indicative of a gaze direction and/or a convergence distance. The head-mounted device 1010 is further able to apply a first colour rendering mode in a first area 340 of the displaying device 1015 and applying a second colour rendering mode in the second area 350, 360 of the displaying device 1015. The first colour rendering mode and the second colour rendering mode differ in relation to a degree of selective adaptation of intensity of light of wavelengths relevant to the circadian rhythm of a user of the head-mounted device 1015 in accordance with embodiments described in relation to FIGS. 4a, 4b and 4c. Preferably, the head-mounted device 1010 comprises one eye tracker for each eye.

The displaying device 1015 may for example be 3D display, such as a stereoscopic display. The 3D display may for example be comprised glasses equipped with AR functionality. Further, the 3D display may be a volumetric 3D display, being either autostereoscopic or automultiscopic, which may indicate that they create 3D imagery visible to an unaided eye, without requiring stereo goggles or stereo head-mounted displays. Consequently, as described in relation to FIG. 6a, the 3D display may be part of the head-mounted device 1010.

FIG. 6b shows a remote display system 1020 according to one or more embodiments comprising a display device 1015. The remote display system 1020 typically comprises a remote display device 1015. The display device 1015 is remote in the sense that it is not located in the immediate vicinity of the user 1000. The remote display system 1020 is configured for applying adapted colour rendering in relation to intensity of light of wavelengths relevant to the circadian rhythm of a user, e.g. according to the embodiments of the method according to the present disclosure may be performed as disclosed in relation to FIGS. 4a, 4b and 4c. For example, the remote display system 1020 is configured to provide eye tracker functionality by a gaze tracking signal using one or more gaze tracking sensors 1025, e.g. indicative of a gaze direction and/or a convergence distance. In other words, the remote display system 1020 is configured to provide an indication of an object the user 1000 is looking at and/or a depth at which the user is looking/watching. The remote display system 1020 is further able to apply a first colour rendering mode in a first area 340 of the displaying device 1015 and applying a second colour rendering mode in the second area 350, 360 of the displaying device 1015. The first colour rendering mode and the second colour rendering mode differ in relation to a degree of selective adaptation of intensity of light of wavelengths relevant to the circadian rhythm of a user of the head-mounted display in accordance with embodiments described in relation to FIGS. 1*a*-*c* and 2. The remote display 1015 may be a 3D display that does not require stereo/stereoscopic goggles or a 3D display where stereoscopic glasses are needed to visualize the 3D effect to the user. The remote display 1015 may also be a 2D display. The remote display system 1020 may comprise only one eye tracker for both eyes. In other words, the illuminator(s) and the image device(s) are arranged to illuminate/read both eyes of the user.

A person skilled in the art realizes that the present invention is by no means limited to the embodiments described above. On the contrary, many modifications and variations are possible within the scope of the appended claims.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The terminology used herein is for the purpose of describing particular aspects of the disclosure only, and is not intended to limit the invention. The division of tasks between functional units referred to in the present disclosure does not necessarily correspond to the division into physical units; to the contrary, one physical component may have multiple functionalities, and one task may be carried out in a distributed fashion, by several physical components in cooperation. A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems. The mere fact that certain measures/features are recited in mutually different dependent claims does not indicate that a combination of these measures/features cannot be used to advantage. Method steps need not necessarily be performed in the order in which they appear in the claims or in the embodiments described herein, unless it is explicitly described that a certain order is required. Any reference signs in the claims should not be construed as limiting the scope.

The invention claimed is:

1. A method in a system comprising a display for applying adapted colour rendering in relation to the intensity of light of wavelengths relevant to the circadian rhythm of a user of the system, the method comprising:
   receiving gaze tracking information identifying a gaze vector of the user of the system;
   determining a respective location of a first area of the display and a second area of the display based on the identified gaze vector;
   applying a first colour rendering mode in the first area of the display; and
   applying a second colour rendering mode in the second area of the display,
   wherein the first colour rendering mode and the second colour rendering mode differ in relation to a degree of selective adaptation of intensity of light of wavelengths relevant to the circadian rhythm of the user,
   wherein the first area of the display is located inside a border angle from the gaze vector and the second area of the display is located outside the border angle from the gaze vector, and
   wherein the second colour rendering mode involves selective adaption of intensity of light of wavelengths relevant to the circadian rhythm to a largest degree at a peak angle from the gaze vector larger than the border angle, and
   wherein the peak angle is within a range of two to five degrees (2-5°).

2. The method according to claim 1, wherein the respective degree of selective adaption for the first area and the second area is based on an effect that selective adaption of light of wavelengths relevant to the circadian rhythm will have on the circadian rhythm when projecting on corresponding area of a retina of an eye of the user.

3. The method according to claim 1, wherein the first colour rendering mode involves no selective adaption of intensity of light of wavelengths relevant to the circadian rhythm.

4. The method according to claim 1, wherein the second area is an entire area of the display outside the border angle from the gaze vector.

5. The method according to claim 1, wherein the second area is an entire area of the display outside the border angle from the gaze vector.

6. The method according to claim 1, wherein the second area is an area of the display outside the border angle from the gaze vector and inside an outer angle from the gaze vector larger than the border angle.

7. The method according to claim 6, wherein the outer angle is within a range of two to five degrees (2-5°).

8. The method of claim 7, wherein the outer angle is within a range of ten to sixty degrees (10-60°).

9. The method according to claim 1, wherein the second colour rendering mode involves selective adaptation of the intensity of light of wavelengths relevant to the circadian rhythm to a largest degree at a peak angle from the gaze vector larger than the border angle.

10. The method of claim 1, wherein the border angle is with a range of one half to fifteen degrees)(0.5-15°.

11. The method of claim 10, wherein the border angle is withing a range of two to six degrees (1-10°).

12. The method of claim 10, wherein the border angle is within a range of two to six degrees (2-6°).

13. The method according to claim 1, further comprising: on condition that the first area and the second area are adjacent to each other, apply a smooth transition from the first colour rendering mode to the second colour rendering mode along a border between the first area and the second area.

14. The method of claim 1, wherein selective adaption of intensity of light of wavelengths relevant to the circadian rhythm involves selective increase of intensity during daytime and selective decrease of intensity during nighttime.

15. The method of claim 1, wherein the selective adaption of intensity of light is of wavelengths within a range of 380-500 nanometres.

16. The method of claim 15, wherein selective adaptation of intensity of light is of wavelengths within a range of 440-490 nanometres.

17. The method of claim 1, wherein the peak angle is three and one half degrees (3.5°).

18. A non-transitory computer-readable medium comprising instructions that, when executed by at least one processor, cause the at least one processor to:
receive gaze tracking information identifying a gaze vector of the user of the system;
determine a respective location of a first area of the display and a second area of the display based on the identified gaze vector;
apply a first colour rendering mode in the first area of the display; and
apply a second colour rendering mode in the second area of the display,
wherein the first colour rendering mode and the second colour rendering mode differ in relation to a degree of selective adaptation of intensity of light of wavelengths relevant to the circadian rhythm of the user,
wherein the first area of the display is located inside a border angle from the gaze vector and the second area of the display is located outside the border angle from the gaze vector,
wherein the second colour rendering mode involves selective adaption of intensity of light of wavelengths relevant to the circadian rhythm to a largest degree at a peak angle from the gaze vector larger than the border angle, and
wherein the peak angle is within a range of two to five degrees (2-5°).

19. A system for applying adapted colour rendering in relation to intensity of light of wavelengths relevant to the circadian rhythm of a user of the system, the system comprising:
a display;
a processor; and
a memory, said memory containing instructions executable by said processor, whereby said system is operative to:
receive gaze tracking information identifying a gaze vector of the user of the system;
determine a respective location of a first area of the display and a second area of the display based on the identified gaze vector;
apply a first colour rendering mode in the first area of the display; and
apply a second colour rendering mode in the second area of the display,
wherein the first colour rendering mode and the second colour rendering mode differ in relation to a degree of selective adaptation of intensity of light of wavelengths relevant to the circadian rhythm of the user,
wherein the first area of the display is located inside a border angle from the gaze vector and the second area of the display is located outside the border angle from the gaze vector,
wherein the second colour rendering mode involves selective adaption of intensity of light of wavelengths relevant to the circadian rhythm to a largest degree at a peak angle from the gaze vector larger than the border angle, and
wherein the peak angle is within a range of two to five degrees (2-5°).

20. The system according to claim 19, wherein the respective degree of selective adaptation for the first area and the second area is based on an effect that selective adaptation of light of wavelengths relevant to the circadian rhythm will have on the circadian rhythm when projected on corresponding areas of a retina of an eye of the user.

21. The system according to claim 19, wherein the first area of the display is located inside a border angle from the gaze vector and the second area of the display is located outside the border angle from the gaze vector, and wherein the second colour rendering mode involves a higher degree of selective adaptation of intensity of light of wavelengths relevant to the circadian rhythm than the first colour rendering mode.

22. The system of claim 19, wherein the system further comprises a head mounted device, wherein the head mounted device comprises the display, the processor, and the memory.

* * * * *